United States Patent [19]

Hutson, Jr.

[11] 4,275,257

[45] Jun. 23, 1981

[54] ISOMERIZATION OF HYDROCARBON FEED

[75] Inventor: Thomas Hutson, Jr., Bartlesville, Okla.

[73] Assignee: Phillips Petroleum Company, Bartlesville, Okla.

[21] Appl. No.: 117,131

[22] Filed: Jan. 31, 1980

[51] Int. Cl.³ .............................................. C07C 5/13
[52] U.S. Cl. .................................. 585/738; 585/372; 585/741
[58] Field of Search ...................... 585/372, 738, 741

[56] References Cited

U.S. PATENT DOCUMENTS

| | | | |
|---|---|---|---|
| 2,983,774 | 5/1961 | Thompson | 585/741 |
| 3,104,266 | 9/1963 | Kron | 585/738 |
| 3,188,361 | 6/1965 | Cabbage | 585/738 |

Primary Examiner—Curtis R. Davis

[57] ABSTRACT

In a process for isomerizing a hydrocarbon feed in the presence of a metal halide catalyst and a hydrogen halide in which the reaction effluent is separated into a first liquid phase and an uncondensed first vapor phase, including hydrogen halide and noncondensable hydrocarbon gases, the first liquid phase is further separated into a second liquid phase and an uncondensed second vapor phase, including hydrogen halide, the uncondensed second vapor phase is recycled to the isomerization reaction and a portion of the uncondensed first vapor phase is at least intervally removed from the process to prevent buildup of noncondensable hydrocarbon gases in the system, improved operation is attained by passing an absorption liquid including a portion of the second liquid phase, from the second separation, a portion of the hydrocarbon feed or mixtures thereof, through the uncondensed vapor phase prior to venting the latter, to absorb hydrogen halide from the uncondensed first vapor phase, and absorption liquid utilized to absorb hydrogen halide from the uncondensed first vapor phase is recycled to the isomerization reaction.

39 Claims, 1 Drawing Figure

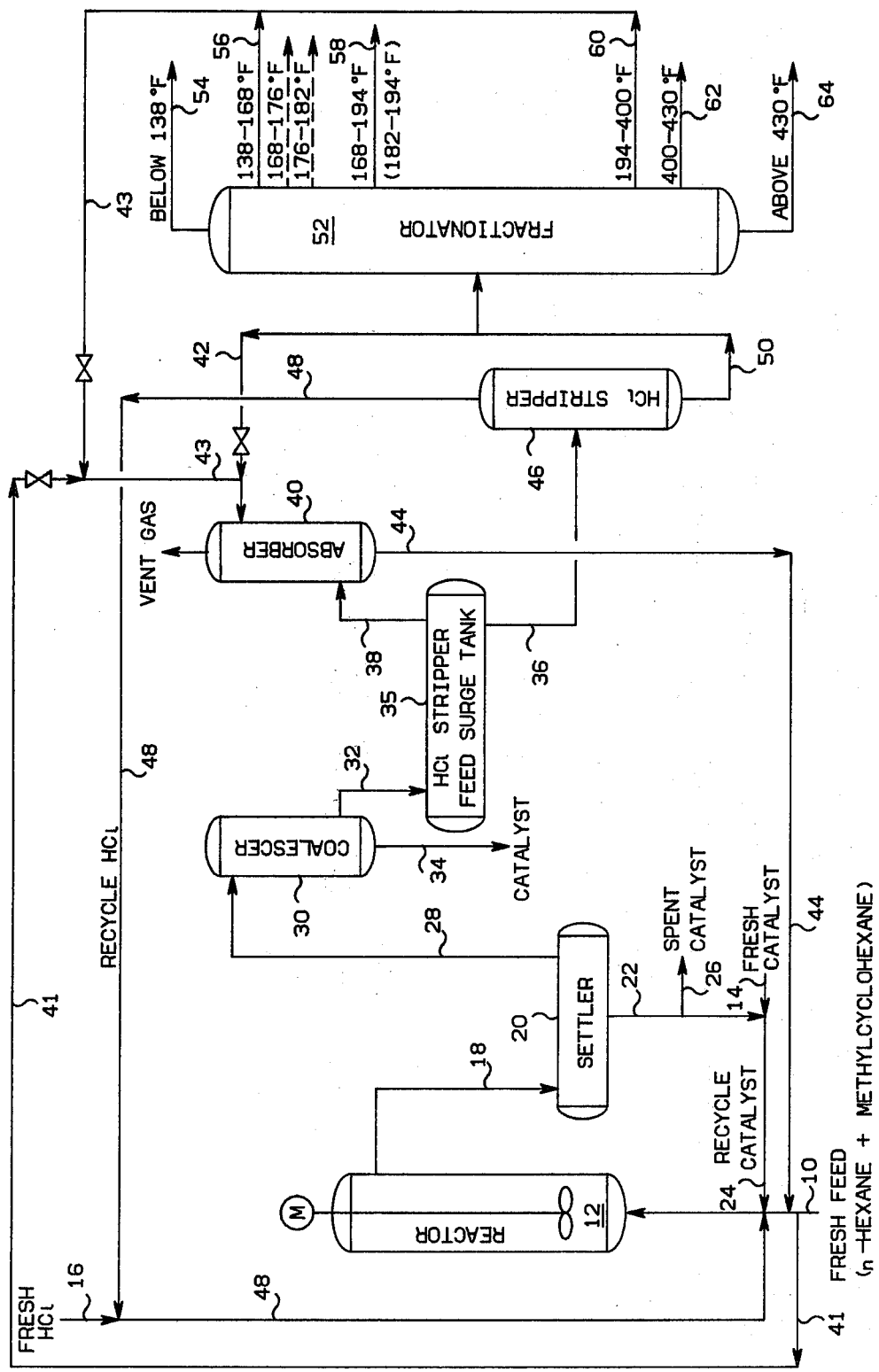

ISOMERIZATION OF HYDROCARBON FEED

The present invention relates to an improved process for the isomerization of hydrocarbons. In a more specific aspect the present invention relates to an improved process for the isomerization of hydrocarbons in the presence of a metal halide catalyst and a hydrogen halide.

Various hydrocarbon fractions of petroleum contain large amounts of naphthenic compounds and normal paraffins. Many of these compounds are relatively useless in their original form. However, such compounds can be converted to valuable materials which are useful in motor fuels, jet fuels or as starting materials for chemical processes. For example, n-hexane which has a low octane number can be converted to certain isohexanes which have a high octane number and thereby form valuable blending stocks for motor fuels. In addition, compounds such as methylcyclopentane can be converted to cyclohexane which can be utilized as a starting material in chemical processes, such as the production of nylon.

In one prior art method, for the conversion of such hydrocarbon fractions, normal paraffins and naphthenes are isomerized in the presence of a metal halide catalyst and a hydrogen halide, such as aluminum chloride and hydrogen chloride. In a conventional isomerization system, hydrocarbon reactants are contacted with the metal halide catalyst in the presence of a hydrogen halide in an isomerization reaction zone and effluent from the reaction zone is passed to a settler where a major portion of the metal halide catalyst is separated and recycled back to the reaction zone. The hydrocarbon portion of the effluent is then subjected to further treatment to remove catalyst fines or entrained droplets, as in a coalescer. Following the removal of catalyst fines the product, which contains a major portion of the hydrogen halide, is generally sent to a surge tank in which fixed gases, including hydrocarbon gases and some of the hydrogen halide, are separated from the liquid portion of the product which also contains substantial amounts of hydrogen chloride. Since the fixed gases contain hydrocarbon gases which tend to build up in the system and which must be removed at least intervally in order to prevent such buildup, these noncondensable gases are generally vented. However, significant amounts of hydrogen halide gas will be lost in this manner, thus requiring substantial volumes of makeup hydrogen halide to be added to the system and, of course, increasing the cost of the operation. To prevent as much as possible of the hydrogen halide from being vented with the hydrocarbon gases it is common practice to mount an absorber on top of the feed surge and to remove as much hydrogen halide as possible from the gases by countercurrent contact with an absorption oil. The absorption oil may be an oil from an outside source but is generally a portion of the hydrocarbon feed to the system and/or a portion of the total hydrocarbon product prior to the hereinafter mentioned fractionation. In such instances, since the absorber is in open communication with the surge tank, the absorption oil drains back into the surge tank and thus dilutes the desired hydrocarbon product in the surge tank with the absorption oil. The hydrocarbon product discharged from the surge tank and containing most of the hydrogen halide is then passed to a hydrogen halide stripper where the hydrogen halide is separated as an overhead and the desired hydrocarbon products are separated as a bottoms. Such a stripper is normally provided with a reboiler. The overhead hydrogen halide is recycled to the isomerization reactor. The bottoms isomerization product from the hydrogen halide stripper is then subjected to fractionation, preferably after aqueous caustic washing, in a number of stages to recover a plurality of different fractions, some of which, particularly unreacted hydrocarbon feed, are recycled back to the isomerization reactor. Low boiling materials, such as isohexanes, are recovered as a blending stock for motor fuels because of their high octane, cyclohexane is recovered as a product for further use in chemical processes and, in some instances, a high boiling end product is recovered as a high density, high energy fuel for use as a jet fuel.

As previously indicated, such conventional isomerization systems result in undesired dilution of the isomerization product with feed to the system or an outside absorption oil. Utilization of a portion of the isomerization product (before fractionation) as an absorption oil removes little hydrogen halide from the vent gases since it has essentially the same composition as the material being separated in the surge tank itself. Thus, particularly in the last instance, such systems also suffer the disadvantage of the loss of substantial volumes of hydrogen halide with the vent gases. Such conventional absorption of hydrogen halide from the vent gases also has a tendency to overload the fractionation system, particularly where a part of the feed and/or an outside absorption oil is employed, thereby requiring larger fractionation facilities than are really necessary or cutting down the ultimate throughput of the system. Finally, conventional fractionation of the isomerization product leaves a great deal to be desired, to the extent that isohexanes of relatively low octane value are removed along with the high octane isohexanes, thereby diluting this product, certain high octane isoheptanes are often recycled to the isomerization reaction with a part of the cyclohexane, are collected in the cyclohexane product or are collected with $C_7$, $C_8$ and $C_9$ naphthenes and recycled to the isomerization reactor. This unnecessary recycle of the high octane materials thus reduces the volume of high octane material recovered and also overloads the system to a certain extent, since further conversion does not take place or these materials are converted to undesirable materials.

It is therefore an object of the present invention to provide an improved process for the isomerization of hydrocarbons which overcomes the above mentioned and other disadvantages of the prior art.

Another object of the present invention is to provide an improved process for the isomerization of hydrocarbons in the presence of a metal halide catalyst and a hydrogen halide.

Still another object of the present invention is to provide an improved process for the isomerization of hydrocarbons in the presence of a metal halide catalyst and a hydrogen halide in which loss of hydrogen halide is reduced.

Yet another object of the present invention is to provide an improved process for the isomerization of hydrocarbons in the presence of a metal halide catalyst and a hydrogen halide in which product dilution is significantly reduced.

Another and further object of the present invention is to provide an improved process for the isomerization of hydrocarbons in which conversion to high value products is increased.

Yet another object of the present invention is to provide an improved process for the isomerization of hydrocarbons wherein conversion to products of high octane number is increased.

A further object of the present invention is to provide an improved process for the isomerization of hydrocarbons in which the recovery of high value products is improved.

A still further object of the present invention is to provide an improved process for the isomerization of hydrocarbons in which overloading of the fractionation system for the separation of the isomerization product is reduced.

Another object of the present invention is to provide an improved process for the isomerization of hydrocarbons in which the size of the fractionation system, utilized to separate the isomerization product, is reduced and/or the throughput for a given size fractionation system is increased.

These and other objects of the present invention will be apparent from the following description.

SUMMARY OF THE INVENTION

In a process for isomerizing a hydrocarbon feed in the presence of a metal halide catalyst and a hydrogen halide in which the reaction effluent is separated into a first liquid phase and an uncondensed first vapor phase, including hydrogen halide and noncondensable hydrocarbon gases, the first liquid phase is further separated into a second liquid phase and an uncondensed second vapor phase, including hydrogen halide, the uncondensed second vapor phase is recycled to the isomerization reaction and a portion of the uncondensed first vapor phase is at least intervally removed from the process to prevent buildup of noncondensable hydrocarbon gases in the system, improved operation is attained by passing an absorption liquid, including a portion of the second liquid phase, from the second separation, a portion of the hydrocarbon feed or mixtures thereof, through the uncondensed first vapor phase prior to venting of the latter, to absorb hydrogen halide from the uncondensed first vapor phase, and the absorption liquid utilized to absorb hydrogen halide from the uncondensed first vapor phase is recycled to the isomerization reaction.

BRIEF DESCRIPTION OF THE DRAWING

The single FIGURE of the drawing is a schematic flow diagram of an isomerization system useful in the practice of the present invention.

DESCRIPTION OF THE PREFERRED EMBODIMENTS

The isomerization method of the present invention is applicable to the conversion of a wide variety of hydrocarbons. For example, straight chain paraffins such as butane, pentane, hexane, heptane and higher molecular weight compounds can be converted to various isomers. Also, moderately branched paraffins can be converted to more highly branched materials. For example, 2-methylpentane can be isomerized to 2,2-dimethylbutane and 2,3-dimethylbutane, both of which have high octane values and are useful as blending stocks for gasolines. In addition, it is possible to isomerize naphthenic hydrocarbons having 4, 5, 6, 7 and more carbon atoms. Examples include the isomerization of methylcyclopentane to cyclohexane; 1,1-dimethylcyclobutane to methylcyclopentane: 1,2-dimethylcyclopentane to methylcyclohexane, etc. In a preferred embodiment, in accordance with the present invention, a mixed feed stream containing a major proportion of n-hexane, significant amounts of methylcyclopentane and isohexanes, lesser amounts of cyclohexane and trace amounts of isoheptanes is utilized. The major products of this mixture are isohexanes, at least some of which are the desired high octane blending stocks, lesser amounts of cyclohexane, which is a valuable feed material for chemical processes, and lesser amounts of isoheptanes which also exhibit high octane numbers. In addition, it is also possible to recover from such a product stream a high density product which may be utilized as a jet fuel.

The isomerization reaction is preferably carried out at a temperature between about 25° C. and about 400° C., at pressures from 1 atmosphere to about 1000 psi or higher and at a liquid hourly space velocities from about 0.1 to about 20.

Catalyst which can be employed in carrying out the isomerization reaction comprise metal halides, such as aluminum chloride, aluminum bromide, boron trifluoride, and the halides of metals such as zinc, tin, arsenic, antimony, zirconium, beryllium, titanium, iron and the like. Such catalysts are especially effective when present as complexes which are formed by interaction between the metal halides and hydrocarbons present in the reaction system. A particularly desirable reaction catalyst is a complex of a hydrocarbon with aluminum chloride. In addition to the catalyst, it is desirable that the corresponding hydrogen halide be present in the reaction system, since this material maintains catalyst activity at a high level. The reaction rate and the conversion of the hydrocarbon feed is dependent on the amount of aluminum chloride in the aluminum chloride-hydrocarbon complex. Thus, to maintain a normal hexane conversion of about 55 percent, the catalyst complex should contain about 60 to 62 percent aluminum chloride. However, the quantity of aluminum chloride in the complex can be varied over wide ranges to provide a corresponding range of feed reactant conversion. While the overall activity of the catalyst is established by the aluminum chloride content, as stated, the presence of hydrogen chloride is required to provide high activity. Broadly, the quantity of hydrogen chloride is between about 2 and about 6 weight percent of the feed with about 4 percent being preferred. The hydrocarbon to catalyst ratio is also an important factor in the isomerization rate and preferably the ratio is between about 0.8/1 and about 1.4/1. Also ratios as high as 5 to 1 can be utilized if the reaction temperatures are increased.

Preferred mixed feeds, such as that referred to above, usually contain a certain amount of contaminants which are desirably removed prior to their introduction into the isomerization reactor. Such contaminants include benzene, sulfur compounds and the like and their removal can be effected by contacting the feed with a hydrogenation nickel catalyst and hydrogen under suitable conditions, such as between about 360° and about 500° F. Pressure does not appreciably affect the hydrogenation reaction and the actual pressure employed is established principally by the partial pressure of the hydrogen present. As a result of this hydrogenation, benzene is converted to cyclohexane which is one of the desired end materials of the present process. The sulfur compounds react with $H_2$ in the presence of a nickel catalyst to form $H_2S$ which is removed from the reaction product. It is also desirable that the feed be dehydrated as by passing the same through a conventional dehydrator.

While various means can also be utilized, in conjunction with the present process, to form the catalyst complex prior to introduction into the isomerization reactor, the invention will be described in the context that the hydrocarbon feed and the catalyst are charged directly to the reactor.

It is to be understood, however, that such pretreatments and preformation of a catalyst complex can be utilized in practicing the present invention.

The present invention will be best understood by reference to the drawing, which is a flow diagram, in schematic form, showing apparatus useful in the practice of the present method. In describing the method of the present invention with relation to the drawings, reference will be made to the preferred embodiment of the present invention, in which a mixed feed containing a major portion, for example, about 50 to 70 percent by volume of normal hexane, about 15 to about 20 volume percent of methylcyclopentane, about 13 to about 15 volume percent of isohexanes, about 3 to 4.5% cyclohexane, and about 0.1 to about 2.5 volume percent of isoheptanes.

In accordance with the FIGURE the feed mixture is introduced through line 10 to isomerization reactor 12. The isomerization reactor is preferably provided with a motor driven stirrer. Fresh catalyst, such as aluminum chloride, for startup of the process and for makeup during operation of the process, may be introduced through line 14. Fresh hydrogen halide, in this case hydrogen chloride, may be introduced to the system, for startup of the process and for makeup during operation of the process, through line 16. Both the fresh catalyst and the fresh HCl will be relatively minimal during the actual operation, necessitated only by withdrawal of spent catalyst from the system and HCl losses during operation of the system. Products of the isomerization reaction are discharged from reactor 12 through line 18. The isomerization effluent, which includes both the catalyst and the hydrogen halide, is passed to a settler 20 for separation of the catalyst from the isomerization reaction product. Separated catalyst from settler 20 is withdrawn through line 22 and is recycled to the reaction zone 12 through line 24. At least intervally it is necessary to remove spent catalyst from the system and such removal may be carried out by withdrawal through line 26. Isomerization product substantially free of catalyst is withdrawn from the settler 20 through line 28. The reaction products passing through line 28 are then passed to a suitable means for separating entrained catalyst droplets from the isomerization product. In the present case a coalescer 30 is shown. The isomerization product from coalescer 30 is discharged through line 32 and to the extent the coalesced catalyst is to be withdrawn for recovery of the components or disposal, such withdrawal is carried out through line 34. Various inert materials can be used for coalescing a catalyst including sand, charcoal and the like. However, bauxite is a preferred material for this purpose.

The effluent from coalescer 30, passing through line 32, is substantially free of entrained catalyst complex but contains dissolved aluminum chloride and the bulk of the hydrogen chloride. This effluent is fed to a hydrogen chloride stripper feed surge tank 35. In HCl stripper feed surge tank 35 noncondensable gases, such as hydrocarbon gases, are separated from the isomerization product. The isomerization product from feed surge tank 35 is discharged through line 36. As previously indicated, the buildup of noncondensable hydrocarbon gases in the system is undesirable and it is necessary to at least intervally vent such gases. However, such gases also contain significant amounts of hydrogen chloride and, therefore, it is highly desirable that the hydrogen chloride be recovered from the gases prior to venting such gases. As previously indicated, it has been the practice in the prior art to mount an absorber on the top of the feed surge tank and to contact the vent gas with a portion of the hydrocarbon feed and/or an outside absorption oil and/or a portion of the separated isomerization product to recover HCl. In such arrangements the absorption medium drains back into the feed surge tank and is discharged along with the separated isomerization product through line 36. This has a number of disadvantages as previously pointed out. Consequently, in accordance with the present invention, vent gases, including HCl, are discharged from feed surge tank 35 through line 38 and are fed to a separate absorber unit 40.

The absorption oil may be a portion of the hydrocarbon feed to the isomerization reactor, supplied through line 41; a portion of the isomerization product, prior to the hereinafter mentioned fractionation of the product, supplied through line 42; preferably, in accordance with another novel aspect of the present invention, a selected fraction of the isomerization product, obtained by the hereinafter mentioned fractionation, supplied through line 43; or any combination of two or more of these streams.

In contrast to conventional operations, in accordance with the present invention, the absorption media, containing absorbed HCl, is discharged from absorber 40 through line 44 and is recycled back to reactor 12. As will be pointed out in more detail hereinafter, recycle of the absorption medium, containing recovered hydrogen chloride, back to the reactor, has a number of advantages, including; reducing the load on the fractionation system, which is used to separate isomerization products, and this recycle plus utilization of the preferred absorption medium increases the conversion of less desirable isomerization products into more highly desirable products.

The isomerization product from feed surge tank 35 passing through line 36, is sent to a hydrogen chloride stripper 46. In hydrogen chloride stripper 46, hydrogen chloride is separated from the isomerization product and is recycled to the reactor through line 48. The separated isomerization product, discharged from hydrogen chloride stripper 46, is substantially free of catalyst and hydrogen chloride and is discharged as a bottoms product through line 50. As previously indicated, a portion of this bottoms product may be used as absorption oil through line 42. The separated isomerization product passing through line 50 is then fractionated in order to separate desired products from unreacted feed materials and less desirable isomerization products. The fractionation system is shown, for simplification, as a single fractionator column 52. However, the fractionation system may comprise a plurality of individual columns connected in series, whose number will depend upon the number of fractions to be separated from the product. A more desirable fractionation system would include two or more multitray fractionation columns designed to provide precise fractionation and thus narrow boiling range fractions. The product passing through line 50 contains a wide variety of individual products. The following table illustrates a typical isomerization product obtained from the isomerization of a feed mixture, such as that previously described. The table lists the predominant individual hydrocarbons together with their boiling points and their motor octane rating (where known).

| Octane | Component | Atmospheric Boiling Point °F. | °C. |
|---|---|---|---|
|  | C$_6$ Alkanes |  |  |
| 93.4 m | 2,2-DM Butane (Neohexane) | 121.5 | 49.7 |
| 94.3 m | 2,3-DM Butane (Diisopropyl) | 136.4 | 58.0 |
| 73 m | 2-M pentane | 140.5 | 60.3 |
| 75 m | 3-M pentane | 145.9 | 63.3 |
| 26 m | n-Hexane (unreacted) | 155.7 | 68.7 |
|  | C$_6$ Naphthenes |  |  |
| 80 m | Methylcyclopentane (unreacted) | 161.3 | 71.8 |
|  | Isoheptanes |  |  |
| 93 m | 2,2-DM pentane | 174.7 | 79.3 |
| 82 m | 2,4-DM pentane | 177.1 | 80.6 |
|  | Cyclohexane |  |  |
| 78.6 m | Cyclohexane (Product) | 177.3 | 80.7 |
|  | Isoheptane |  |  |
| 84 m | 3,3-DM pentane | 187.0 | 86.1 |
|  | C$_7$ Naphthenes |  |  |
| none known | 1,1-DM Cyclopentane | 189.5 | 87.5 |
|  | C$_7$ Alkanes |  |  |
| 89.0 m | 2,3-DM pentane | 193.6 | 89.8 |
| 45 m | 2-M hexane | 194.2 | 90.1 |
| not known | 3-M hexane | 197.4 | 91.9 |
| not known | 3-E pentane | 200.3 | 93.5 |
| 0 | n-Heptane | 209.1 | 98.4 |
|  | C$_7$ Naphthenes |  |  |
| 73 m | M cyclohexane | 213.4 | 100.8 |
|  | E cyclopentane | 217.4 | 103.0 |
|  | C$_8$ Naphthenes |  |  |
| 62.2 m | trans 1,4-DM cyclohexane | 247.3 | 119.6 |
| not known | 1,1 DM cyclohexane | 247.3 | 119.7 |
|  |  |  | 119.8 |
| not known | trans 1,3-DM cyclohexane | 249.3 | 120.7 |
| 78.7 m | trans 1,2-DM cyclohexane | 254.7 | 123.7 |
| 68.2 m | cis 1,4-DM cyclohexane | 256.1 | 124.5 |
| 71 m | cis 1,3-DM cyclohexane | 256.6 | 124.7 |
| 78.6 m | cis 1,2-DM cyclohexane | 266.2 | 130.1 |
| 40.8 m | E cyclohexane | 266.7 | 130.4 |
| 28.1 m | P cyclopentane | 267.4 | 130.8 |
|  | C$_9$ Naphthenes Plus |  |  |
| not known | 1,3,5-TriM cyclohexane | 284.0 | 140.0 |
|  |  | 284.9 | 140.5 |
| 61.1 m | Iso P cyclopentane | 309.9 | 154.4 |
|  | D M Bicyclodecanes | 380 | 193.3 |
|  |  | 470 | 243.5 |
|  | D M Bicyclodecanes | 400 | 204.4 |
|  |  | 430 | 221.1 |
|  | D M Bicyclodecanes | 415 | 212.7 |
|  |  | 428 | 220.0 |

DM = dimethyl
M = methyl
E = ethyl
P = propyl
m = motor method octane number

Generally this product will contain about 15 to about 17 percent by volume of unreacted n-hexane, about 2 to 3 percent of unreacted methylcyclopentane, about 9 to 10 percent of cyclohexane, about 25 to 30 percent isohexanes, about 0.1 to 2 percent of isoheptanes and smaller amounts of C$_7$, C$_8$ and C$_9$ naphthenes.

As previously indicated, it has been the normal practice in the prior art to recover a fraction including all isohexanes as a product for use as a high octane blending stock for gasolines. However, as is apparent from the previous table, only 2,2-dimethylbutane(neohexane) and 2,3-dimethylbutane (diisopropyl) have desirably high octane ratings whereas 2-methylpentane and 3-methylpentane and like monosubstituted isohexanes have relatively poor octane ratings. Consequently, in accordance with the present invention, an overhead product from fractionator 52 is withdrawn as a product boiling below about 138° F. This product is discharged through line 54. Accordingly, only the major portion of 2,2-dimethylbutane and 2,3-dimethylbutane will be included in this product fraction and the lower octane isohexanes will be excluded to the extent possible. A side cut boiling between about 138° and 168° F. is withdrawn through line 56 and passed through line 42 as an absorption medium for use in absorber 40. This fraction preferably includes the monosubstituted isohexanes, unreacted n-hexane and unreacted methylcyclopentane. A second side cut boiling between about 168° and 194° F. is recovered through line 58. This fraction contains the desired product cyclohexane, the majority of the disubstituted isopentanes and a small amount of disubstituted C$_7$ naphthenes. A third sidecut boiling between about 194° and 400° F., which includes the remainder of the isoheptanes, primarily monosubstituted isoheptanes, n-heptane, C$_7$ naphthenes, C$_8$ naphthenes and C$_9$ naphthenes, is withdrawn through line 60 and is added to the sidecut passing through line 56 and fed to absorber 40 through line 42. By thus utilizing the two sidecuts boiling between about 138° and 168° F. and 194° F. and 400° F. respectively, particularly the former, as an absorption medium and then recycling this absorption medium to the reactor through line 44, monosubstituted isomers of relatively low octane rating will be converted to higher octane disubstituted isomers. For example, the monosubstituted isohexanes will be converted to disubstituted isohexanes, particularly neohexane, and diisopentanes which also have relatively high octane ratings. Also by utilizing this particular material as an absorption medium in absorber 40, the volume of absorber medium is reduced, and the amount of hydrogen chloride absorbed from the vent gas is significantly increased due to the fact that this material is a better absorption medium than the feed material (which can be supplied through line 41) or the total separated product from the isomerization reaction from the hydrogen chloride stripper (which can be supplied through line 42). Operation in this manner also significantly increases the conversion of low octane rating materials to high octane rating materials by virtue of the recycle of the absorber bottoms through line 44 to isomerization reactor 12. By the same token this recycle also reduces the ultimate cost of fractionation by either reducing the size of the fractionation system necessary or increasing the throughput of the system to a fractionation system of a given size. Obviously this reduction in fractionation system cost is attributable to the fact that no absorption medium passes to the fractionation system and thus there is no dilution of the isomerization product passing through line 50 to fractionation system 52.

The isomerization product boiling above about 380° to 400° F. also contains significant amounts of a high density material which, in accordance with the prior art, has been found to be valuable as a high energy fuel for turbojet engines, ramjets and liquid fuel rocket engines and may be substituted for the conventional JP4 and JP6 grades of fuels. These desired materials comprise primarily dimethylbicyclodecanes boiling between about 415° F. and about 428° F. Consequently, a major portion of these materials may be recovered by removing a sidecut boiling between about 380° or 400° F. and about 430° F. through line 62. In this instance a bottom fraction boiling above about 430° F. would be recovered through line 64. This latter fraction could also be added to the absorption medium being passed through line 42 and ultimately recycled back to the reactor through line 44. In an alternative operation, the entire fraction boiling above about 380° or 400° F. could be recovered as a bottoms fraction and utilized as a high density fuel. In still another embodiment all of the material boiling above about 194° F. could be removed as a bottoms product and utilized as part of the absorption medium passing through line 42 to absorber 40.

Where the content of disubstituted isoheptanes in the isomerization product is sufficiently high that a precise fractionation can be justified or a higher purity cyclohexane product is desired and can be economically justified, an alternative procedure would separate materials boiling between about 168° and 194° F. into a plurality of separate cuts. For example a fraction boiling between about 168° and about 176° F. could be withdrawn as a product sidecut. This fraction would contain a substantial portion of high octane 2,2-dimethylpentane. Another sidecut boiling between about 176° F. and about 182° F. would be recovered as the cyclohexane product, hence the cyclohexane product would contain at most the 2,4-dimethylpentane. The third sidecut withdrawn through line 58 would then include material boiling between about 182° F. and about 194° F. and would include 3,3-dimethylpentane and 2,3-dimethylpentane, both of which have relatively high octane ratings and which could be utilized as a blending stock in gasolines.

While specific materials, specific items of equipment, specific modes of operation and specific conditions of operation have been referred to herein by way of example, it is to be understood that these specific details are given for illustrative purposes only and are not to be considered limiting.

I claim:

1. In an isomerization process for isomerizing a hydrocarbon feed, including; isomerizing said hydrocarbon feed, in an isomerization reaction step, in the presence of a metal halide catalyst and a hydrogen halide; separating the reaction effluent from said isomerization reaction step, in a first separation step, into a first liquid phase and an uncondensed first vapor phase, containing a significant amount of said hydrogen halide and noncondensable hydrocarbon gases; further separating the thus separated first liquid phase, in a second separation step, into a second liquid phase and an uncondensed second vapor phase, containing a major portion of said hydrogen halide; recycling the thus separated second vapor phase, in a first recycling step, to said isomerization reaction step; fractionating at least a portion of said second liquid phase, in at least one fractionation step, to produce a plurality of liquid fractions; and at least intervally removing at least a portion of the thus separated first vapor phase from said isomerization process, in a vapor phase removal step, to reduce the buildup of said noncondensible hydrocarbon gases in said isomerization process, the improvement comprising:

(a) contacting said uncondensed first vapor phase, in an absorption step subsequent to and separate from said first separation step, with an absorption liquid selected from the group consisting of a portion of said hydrocarbon feed, a portion of said second liquid phase, at least one of said plurality of fractions and mixtures thereof, to absorb at least a portion of the hydrogen halide contained in said uncondensed first vapor phase and produce a third liquid phase containing a major portion of said absorption liquid and the thus absorbed at least a portion of the hydrogen halide contained in said uncondensed first vapor phase and an uncondensed third vapor phase containing a major portion of said noncondensable hydrocarbon gases;

(b) recycling said third liquid phase to said isomerization reaction step, in a second recycling step; and (c) at least intervally removing said uncondensed third vapor phase from said isomerization process, in said vapor phase removal step.

2. A method in accordance with claim 1 wherein the first separation step is carried out in a surge zone.

3. A process in accordance with claim 1 wherein the absorption liquid is a portion of the hydrocarbon feed.

4. A process in accordance with claim 1 wherein the absorption liquid is a portion of the second liquid phase.

5. A process in accordance with claim 1 wherein the absorption liquid is at least one of the plurality of liquid fractions thus produced in the at least one fractionation step.

6. A process in accordance with claim 1 wherein the absorption liquid is a mixture of at least two of a portion of the hydrocarbon feed, a portion of the second liquid phase and at least one of the plurality of liquid fractions thus produced in the at least one fractionation step.

7. A process in accordance with claim 1 wherein the plurality of liquid phase fractions thus produced in the at least one fractionation step comprise a low boiling first liquid fraction, a second liquid fraction having an initial boiling point above the end boiling point of said first liquid fraction, a third liquid fraction having an initial boiling point above the end boiling point of said second liquid fraction and a fourth liquid fraction having an initial boiling point above the end boiling point of said third liquid fraction; and said first liquid fraction, said third liquid fraction and at least a portion of said fourth liquid fraction are recovered as products of said isomerization process.

8. A process in accordance with claim 7 wherein the second liquid fraction is utilized as the absorption liquid.

9. A process in accordance with claim 8 wherein the second liquid fraction is the only liquid utilized as the absorption liquid.

10. A method in accordance with claim 7 wherein the hydrocarbon feed contains constituents adapted to be converted to liquid products of increased octane ratings in the isomerization process.

11. A process in accordance with claim 10 wherein the third liquid fraction is further fractionated, in the at least one fractionation step, to produce at least one fifth liquid fraction, comprising those constituents of said third liquid fraction having higher octane ratings, and a sixth liquid fraction, comprising those constituents of said third liquid fraction having lower octane ratings; and said fifth and said sixth liquid fractions are separately recovered as products of the isomerization process.

12. A process in accordance with claim 7 wherein the hydrocarbon feed contains constituents adapted to be converted to a liquid, high density, high energy product in the isomerization process.

13. A process in accordance with claim 12 wherein the fourth liquid fraction is further fractionated, in the at least one fractionation step, to produce a fifth liquid fraction, comprising lower energy, lower density constituents of said at least one fourth liquid fraction and at least one sixth liquid fraction, comprising the high density, high energy constituents of said at least one fourth liquid fraction; and said sixth liquid fraction is recovered as the liquid, high density, high energy product.

14. A process in accordance with claim 12 wherein the fourth liquid fraction is further fractionated, in the at least one fractionation step, to separate a low boiling fifth liquid fraction, an intermediate boiling sixth liquid fraction comprising the high density, high energy constituents of said at least one fourth liquid fraction and a high boiling seventh liquid fraction; and said sixth, which is the liquid, high density, high energy product, and said seventh liquid fractions are separately recovered as products of the isomerization process.

15. A process in accordance with claim 13 or claim 14 wherein the fifth liquid fraction is utilized as at least a portion of the absorption liquid.

16. A process in accordance with claim 7 wherein the hydrocarbon feed is a mixture of hydrocarbons containing n-hexane and methylcyclopentane.

17. A process in accordance with claim 16 wherein the first liquid fraction comprises a major proportion of diisohexanes contained in the thus separated second liquid phase.

18. A process in accordance with claim 16 wherein the second liquid fraction comprises a major proportion of monoisohexanes, unreacted n-hexane and unreacted methylcyclopentane contained in the thus separated second liquid phase.

19. A process in accordance with claim 16 wherein the third liquid fraction comprises a major proportion of disubstituted pentanes, cyclohexane, and $C_7$ naphthenes contained in the thus separated second liquid phase.

20. A process in accordance with claim 19 wherein the third liquid fraction is further fractionated, in the at least one fractionation step, to produce at least one fifth liquid fraction comprising a major proportion to disubstituted pentanes contained in the thus separated second liquid phase and a sixth liquid fraction comprising a major proportion of cyclohexane contained in said separated second liquid phase; and said at least one fifth and said sixth liquid fractions are separately recovered as products of the isomerization process.

21. A process in accordance with claim 19 wherein the at least one third liquid fraction is further fractionated, in the at least one fractionation step, to produce a low boiling fifth liquid fraction, comprising a major proportion of lower boiling disubstituted pentanes contained in the thus separated second liquid phase, an intermediate boiling sixth liquid fraction comprising a major proportion of cyclohexane contained in said separated second liquid phase, and a high boiling seventh liquid fraction, comprising a major proportion of higher boiling disubstituted pentanes and lower boiling $C_7$ naphthenes contained in said separated second liquid phase; and said fifth, sixth and seventh liquid fractions are separately recovered as products of the isomerization process.

22. A process in accordance with claim 7 wherein the fourth liquid fraction comprises a major proportion of monoisoheptanes, n-heptane, higher boiling $C_7$ naphthenes, $C_8$ naphthenes, $C_9$ naphthenes, didiobicyclodecanes and hydrocarbons boiling above $C_9$ naphthenes contained in the thus separated second liquid phase.

23. A process in accordance with claim 22 wherein the fourth liquid fraction is further fractionated, in the at least one fractionation step, to separate a fifth liquid fraction, comprising a major proportion of the monoisoheptanes, the n-heptane, the higher boiling $C_7$ naphthenes, the $C_8$ naphthenes and the $C_9$ naphthenes contained in the thus separated second liquid phase and at least one sixth liquid fraction, comprising a major proportion of the diisobicyclodecanes and the hydrocarbons boiling above $C_9$ naphthenes contained in said separated second liquid phase; and said at least one sixth liquid fraction is recovered as a product of the isomerization process.

24. A process in accordance with claim 22 wherein the fourth liquid fraction is further fractionated, in the at least one fractionation step, to separate a low boiling fifth liquid fraction, comprising a major portion of the monoisoheptanes, the n-heptane, the higher boiling $C_7$ naphthenes, the $C_8$ naphthenes and the $C_9$ naphthenes contained in the thus separated second liquid phase, an intermediate boiling sixth liquid fraction, comprising the lower boiling diisobicyclodecanes contained in said separated second liquid phase and a high boiling seventh liquid fraction, comprising the higher boiling diisobicyclodecanes and the hydrocarbons boiling above $C_9$ naphthenes contained in said separated second liquid phase; and said sixth and seventh liquid fractions are separately recovered as products of the isomerization process.

25. A process in accordance with claim 23 or claim 24 wherein the fifth liquid fraction is utilized as at least a portion of the absorption liquid.

26. A process in accordance with claim 16 wherein the first liquid fraction has an end boiling point of about 138° F.

27. A process in accordance with claim 16 wherein the second liquid fraction has an initial boiling point above about 138° F. and an end boiling point of about 168° F.

28. A process in accordance with claim 16 wherein the third liquid fraction has an initial boiling point above about 168° and an end boiling point of about 194° F.

29. A process in accordance with claim 28 wherein the third liquid fraction is further fractionated, in the at least one fractionation step, to produce a fifth liquid fraction having an initial boiling point above about 168° F. and an end boiling point of about 176° F., a sixth liquid fraction having an initial boiling point above about 176° F. and an end boiling point of about 182° F. and a seventh liquid fraction having an initial boiling point above about 182° F. and an end boiling point of about 194° F.; and said fifth, sixth and seventh liquid fractions are separately recovered as products of the isomerization process.

30. A process in accordance with claim 16 wherein the one fourth liquid fraction has an initial boiling point above about 194° F.

31. A process in accordance with claim 30 wherein the fourth liquid fraction is further fractionated, in the at least one fractionation step, to produce a fifth liquid fraction having an initial boiling point above about 194° F. and an end boiling point of about 400° F., and at least one sixth liquid fraction having an initial boiling point above about 400° F.; and said at least one sixth liquid fraction is recovered as a product of the isomerization process.

32. A process in accordance with claim 30 wherein the fourth liquid fraction is still further fractionated, in the at least one fractionation step, to separate a fifth liquid fraction having an initial boiling point above about 194° F. and an end boiling point of about 400° F., a sixth liquid fraction having an initial boiling point above about 400° F. and an end boiling point of about 430° F. and a seventh liquid fraction having an initial boiling point above about 430° F.; and said sixth and seventh liquid fractions are recovered as products of the isomerization process.

33. A process in accordance with claim 31 or claim 32 wherein the fifth liquid fraction is utilized as at least a portion of the absorption liquid.

34. A process in accordance with claim 30 wherein the fourth liquid fraction is further fractionated, in the at least one fractionation step, to produce a fifth liquid fraction having an initial boiling point above about 194° F. and an end boiling point of about 380° F., and at least one sixth liquid fraction having an initial boiling point above about 380° F.; and said at least one sixth liquid fraction is recovered as a product of the isomerization process.

35. A process in accordance with claim 30 wherein the fourth liquid fraction is further fractionated, in the at least one fractionation step, to produce a fifth liquid fraction having an initial boiling point above about 194° F. and an end boiling point of about 380° F., a sixth liquid fraction having an initial boiling point above about 380° F. and an end boiling point of about 430° F., and a seventh liquid fraction having an initial boiling point above about 430° F.; and said sixth and seventh liquid fractions are separately recovered as products of the isomerization process.

36. A process in accordance with claim 34 or 35 wherein the fifth liquid fraction is utilized as at least a part of the absorption liquid.

37. A process in accordance with claim 1 wherein the metal halide catalyst is aluminum chloride and the hydrogen halide is hydrogen chloride.

38. A process in accordance with claim 1 wherein the absorption liquid, which is contacted with the uncondensed first vapor stream, is passed through said uncondensed first vapor stream in countercurrent contact therewith.

39. A process in accordance with claim 38 wherein the uncondensed first vapor stream is passed upwardly through an absorption zone and the absorption liquid, which is contacted with said uncondensed first vapor stream, is passed downwardly through said absorption zone.

* * * * *